United States Patent [19]

Niznick

[11] Patent Number: 4,645,453
[45] Date of Patent: Feb. 24, 1987

[54] BENDABLE ADAPTER FOR DENTAL IMPLANT

[76] Inventor: Gerald A. Niznick, 18167 Chardon Cir., Encino, Calif. 91316

[21] Appl. No.: 777,965

[22] Filed: Sep. 19, 1985

[51] Int. Cl.⁴ .............................................. A61C 8/00
[52] U.S. Cl. .................................................... 433/173
[58] Field of Search .............. 433/173, 174, 175, 176

[56] References Cited

U.S. PATENT DOCUMENTS

| | | | |
|---|---|---|---|
| 4,109,383 | 8/1978 | Reed et al. | 433/176 |
| 4,195,367 | 4/1980 | Kraus | 433/173 |
| 4,359,318 | 11/1982 | Gittleman | 433/173 |

Primary Examiner—Robert Peshock
Attorney, Agent, or Firm—Kendrick, Netter & Bennett

[57] ABSTRACT

An implant system includes an anchor the accessible end of which is located substantially at the level of the gum tissue at the alveolar crest. A bendable adapter made of titanium or titanium alloy has one end inserted into the accessible anchor socket for rigid connection thereto, and a second distal end projecting into the dental crown region to support a superstructure. The projecting part of the adapter may take various forms. It may provide a simple coping upon which a single tooth replacement may be built, or it may provide a socket for connection to companion structures. The intermediate portion of the adapter is necked down to provide a bendable region close to the level of the gum tissue whereby the anchor can be positioned for maximum retention, and the projecting end can be positioned to avoid tissue interference, to achieve parallelism for detachable connectors, to achieve maximum occlusal and esthetic functions. The adapter is made of (1) titanium, (2) a titanium alloy such as that consisting of 90% titanium, 6% aluminum and 4% vanadium, or (3) stainless steel.

17 Claims, 8 Drawing Figures

U.S. Patent    Feb. 24, 1987    Sheet 1 of 2    4,645,453
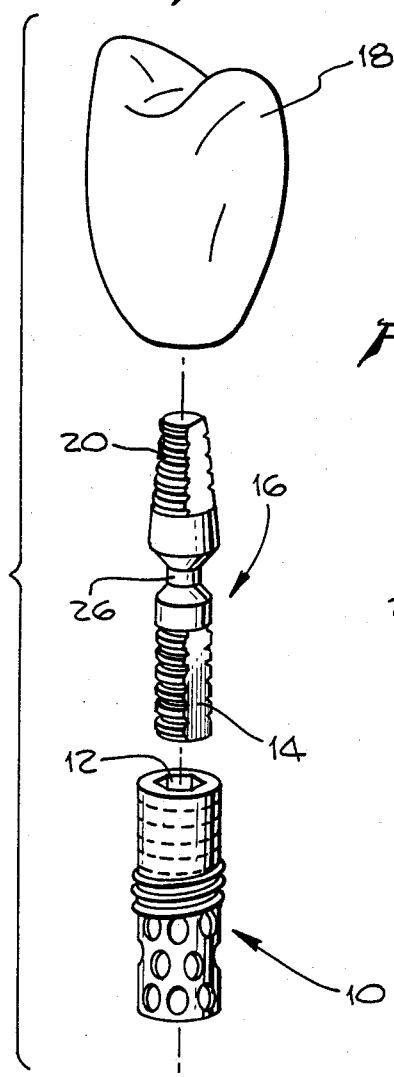
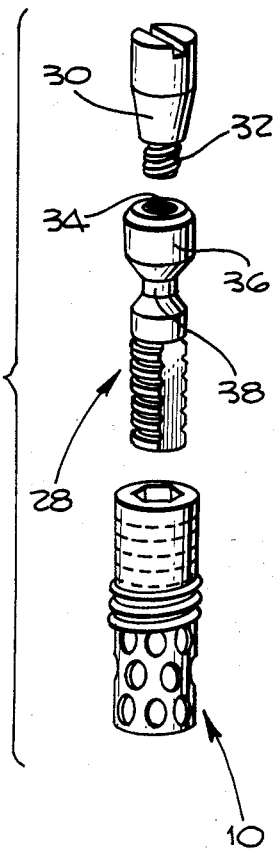
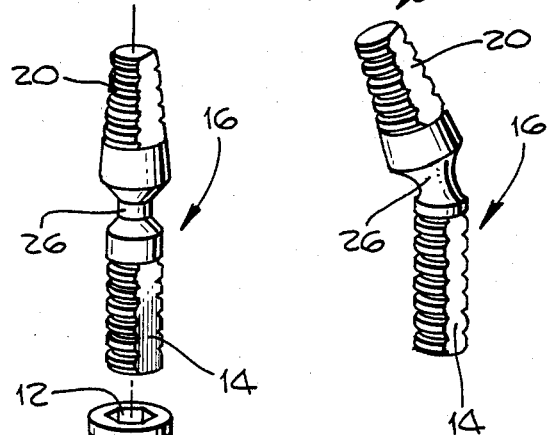
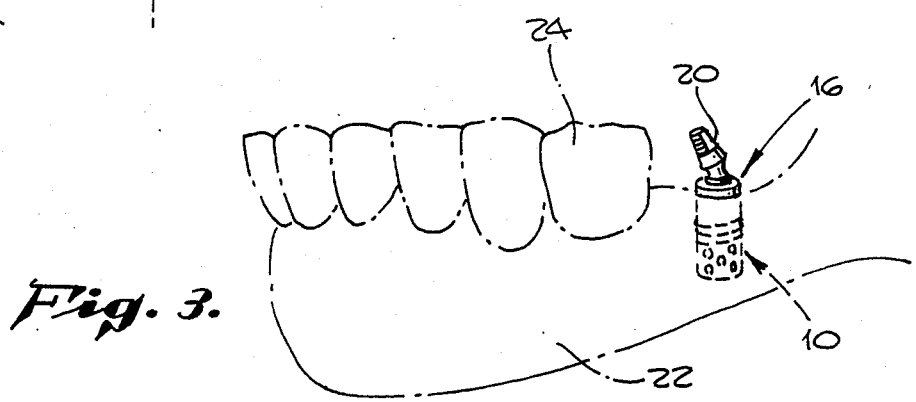

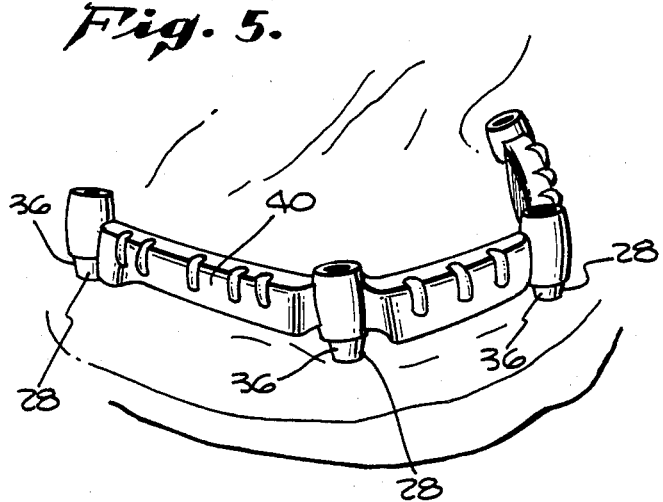
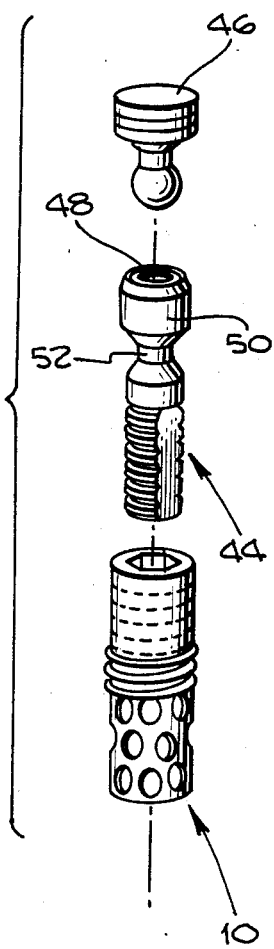
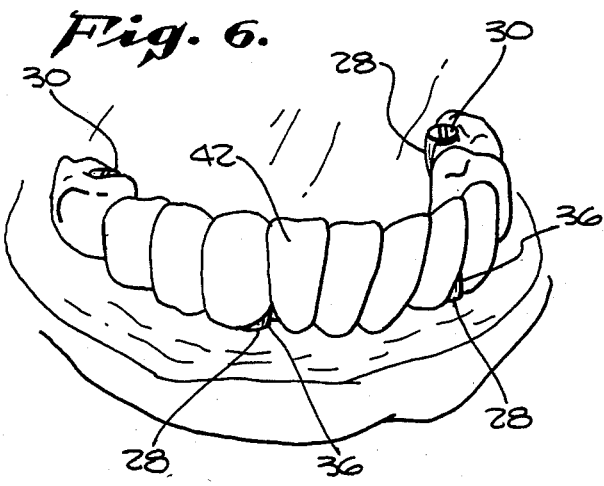
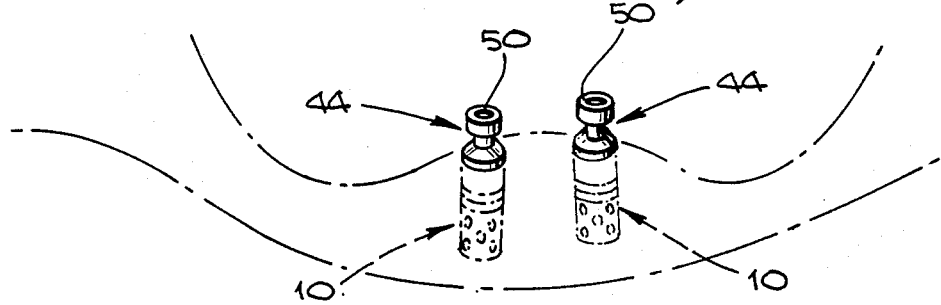

BENDABLE ADAPTER FOR DENTAL IMPLANT

FIELD OF INVENTION

This invention relates to two part dental implants, and more particularly to a titanium adapter cooperable with the anchor at one end and the superstructure at the other.

BACKGROUND OF THE INVENTION

Dental implantology for dental prostheses is now often selected in the interests of (1) achieving stable mechanical structures; (2) minimizing distortions of natural conformation; and (3) promoting comfortable and effective dental functions. The most reliable way to achieve these results is with a two part implant that allows for attachment of an adapter to an anchor. Certain problems remain.

For example, the location and axial orientation of the anchor in the jaw bone is selected after careful radiological survey in order to maximize the prospects for long term retention. Unfortunately, the location and orientation so determined often do not comport with the optimum axial orientation of the superstructure needed for esthetics and dental function. Prior art two part implants have not permitted any adjustments in the angularity of the parts of the implant. Hence compromises have been tolerated. In some cases, the misorientations have been so extreme as to prevent the utilization of removable bridges.

The primary object of the present invention is to provide a two part implant system in which the angular orientation of the prosthesis can be adjusted to maximize esthetic and mechanical requirements while not compromising orientation of the anchor for proper fixation.

SUMMARY OF INVENTION

In order to accomplish the foregoing objective, I provide, first, an anchor that nominally projects slightly above the bone ridge to the level of the gum tissue at the alveolar crest and second, a special bendable adapter made of titanium or titanium alloy. One end of the adapter is inserted into the accessible anchor socket for rigid connection thereto, and the other or distal end projects into the dental crown region to support a superstructure. In a simple case, the projecting end of the adapter is located adjacent a normal tooth and supports a crown. In a more elaborate case, projecting ends of a number of adapters may be oriented to comport with the design of the superstructure and to minimize interference with tissue at the lateral, or even the lingual aspect. In still another case, the projecting ends of a plurality of adapters may provide parallel sockets for a detachable ball connector of an overdenture. The projecting part of the adapter takes various forms for such functions. For example, the projecting part may accommodate a screw, or it may be a simple coping upon which a superstructure can be built, or it may provide the socket for a ball connector.

The intermediate portion of the adapter is necked down to provide a bendable region close to the level of the gum tissue. The bendable region allows the dentist to change the axial alignment of the projecting end of the adapter in order that it closely conforms to the surrounding structures, or to achieve parallelism, as for detachable ball connectors, or to avoid interference with the mouth tissues. In order to achieve bendability without undue compromise of strength, I employ commercially pure titanium or a titanium alloy such as that consisting of 90% titanium, 6% aluminum and 4% vanadium. The pure titanium allows more bending while the alloy exhibits a greater strength characteristic. The neck diameter for pure titanium is between 0.060 to 0.090 inches with about 0.075 inches optimum. The neck diameter for the alloy is between 0.050 and 0.080 inches, with 0.065 inches optimum. Certain stainless steel compositions can be used with adjustments in the neck diameter.

BRIEF DESCRIPTION OF THE DRAWINGS

A detailed description of the invention will be made with reference to the accompanying drawings wherein like numerals designate corresponding parts in the several figures. The mechanical structures shown are to scale.

FIG. 1 is an exploded view of companion implant parts comprising an anchor, a titanium coping adapter and a single tooth restoration to be built on the coping.

FIG. 2 is a pictorial view of a titanium coping adapter bent to justify the different angularity of the anchor and the tooth restoration.

FIG. 3 is a diagrammatic view illustrating the manner in which a coping adapter of FIG. 1 is advantageously used in the mouth of a subject.

FIG. 4 is an exploded view of companion implant parts comprising an anchor, a titanium screw adapter and a screw.

FIGS. 5 and 6 are companion views of the mouth of a subject illustrating the manner in which screw adapters of FIG. 4 are advantageously used (FIG. 5) for attachment of a restoration (FIG. 6).

FIG. 7 is an exploded view of companion implant parts comprising an anchor, a titanium socketed adapter and a ball connector.

FIG. 8 is a diagrammatic view corresponding radiographic projection illustrating the manner in which socketed adapters of FIG. 3 are bent to achieve parallelism for cooperation with a ball connector of a denture structure (not shown).

DETAILED DESCRIPTION OF THE PREFERRED EMBODIMENTS

The following detailed description is of the best presently contemplated mode of carrying out the invention. This description is not to be taken in a limiting sense, but is made merely for purposes of illustrating the general principles of the invention, the scope of the invention being defined by the appended claims.

Structural and operational characteristics attributed to the form of the invention first described shall also be attributed to forms later described, unless such characteristics are obviously inapplicable or unless specific exceptions are made.

In FIG. 1 there is illustrated a biocompatible anchor 10 designed to be attached to the jaw bone of the subject. The anchor 10, described in full detail in my prior U.S. Pat. No. 4,431,416, is installed in a recess prepared in the bone tissue so that its upper end projects about one millimeter above the bone crest. The position and angularity of the anchor is determined primarily by the conformation of the bone tissue.

The present invention is not limited to the specific anchor shown; for example, a blade type anchor can be provided. In any event, the anchor provides a recess 12 for receiving one end 14 of an adapter 16. In the present example, the adapter 16 designed to support a tooth restoration 18 which the dental technician builds upon the projecting or coping end 20 of the adapter 16.

As shown in FIG. 3, the orientation of the anchor 10 as optimally installed in the jaw bone 22 of the subject is tilted considerably relative to the axis of the adjacent tooth 24. If the adapter coping and insert ends 14 and 20 were aligned, then the tooth crown 18 would be quite out of position.

In order to justify the optimum angularity of the crown relative to the angularity of the anchor, the adapter 16 is simply bent in its middle (FIG. 2) to the degree determined by prior study and survey. The transverse axis of bending is determined by a neck 26 formed between the ends of the adapter. The anchor and adapter are sized so that, when installed, the neck 26 is located very close to the upper end of the anchor 10 for maximum justification and minimum strength loss.

The adapter 16 may be made of commercially pure titanium, a titanium alloy or stainless steel so that it is bendable while not compromising its ability to resist and absorb occlusal forces. The pure titanium allows more bending while the alloy exhibits a greater strength characteristic. The practical limits of neck diameter of pure titanium are 0.060 to 0.090 inches with about 0.075 inches optimum. The practical limits of neck diameter for the alloy are 0.050 and 0.080 inches, with 0.065 inches optimum.

In practice, the anchor 10 and the adapter 16 are sized and fitted as necessary for each individual case.

DETAILED DESCRIPTION OF SECOND EMBODIMENT

In FIG. 4 illustrates an implant system comprising the same anchor 10, an adapter 28 and a fastener 30 detachably cooperable with the adapter 28. For this purpose, the fastener 30 has a screw end 32 cooperable with a screw socket 34 at the end of the projecting end or head 36 of the adapter 28. The adapter 28, like the adapter 16, is bendable at its neck 38.

The screw adapter 28 and fastener 30 may be used for a lower jaw restoration such as shown in FIGS. 5 and 6. In FIG. 5, four adapters 28 are secured to embedded anchors (not visible) affixed about the alveolar ridge. Only the lower portions of the adapter heads 36 are visible, the upper portions being hidden by a bar frame casting 40. Denture teeth 42 (FIG. 6) are processed to the bar frame 40. The prosthesis so made is detachably secured to the four adapter heads 36 by four screws 30, two of which are clearly shown in FIG. 6.

In the present case, the screw adapters 28 have been bent in order to achieve maximum conformity to the mouth and to avoid interference with tissues at the lingual and lateral aspects.

DETAILED DESCRIPTION OF THIRD EMBODIMENT

In FIG. 7, there is illustrated the same anchor 10, a socketed titanium adapter 44 and a ball connector 46. The connector 46 is cast into an otherwise conventional overdenture (not shown), and detachably engages the socket 48 at the head 50 of the adapter 44. The mechanical function of the connector is described in detail in U.S. Pat. No. 4,488,875 issued Dec. 18, 1984.

Ideally, two anchor/adapter units are installed in the jaw of the subject in such manner that the anchors are perfectly parallel whereby corresponding parallel installation of connectors in the overdenture achieves simple connection and disconnection. In many cases, optimum installation of the anchors 10 for long term and maximum retention results in nonparallelism as shown in FIG. 8. Nevertheless, the heads can be made parallel by simply bending one of the adapters about its neck 52, or both of the adapters about their necks 52.

Intending to claim all novel, useful and unobvious features and combinations of features shown and/or described, I claim:

1. In a dental implant system:
   (a) an anchor adapted to be secured to the bone tissue at the alveolar ridge of a subject with an orientation determined by case study;
   (b) an adapter having two ends, one end being connected to the anchor and the other end projecting from the anchor;
   said adapter having a straight neck portion located adjacent the top of said anchor, and providing a transverse axis for bending of the projecting end to change the angularity of said projecting end from that of said connected end so that the attitude of said anchor can be selected to maximize retention without compromising desired positioning of a superstructure or a prosthesis adapted to be joined to said projecting end to achieve optimum esthetics and/or function and without distorting, weakening or breaking said neck portion or any other portion of said adapter.

2. The implant system as set forth in claim 1 in which said adapter is made of commercially pure titanium with a neck diameter between 0.060 and 0.090 inches.

3. The implant system as set forth in claim 1 in which said adapter is made of a titanium alloy of about 90% titanium, 6% aluminum and 4% vanadium with a neck diameter between 0.050 and 0.080 inches.

4. The implant system as set forth in claim 1 in which said projecting end of said adapter provides a coping upon which a tooth restoration may be built.

5. The implant system as set forth in claim 1 in which said projecting end of said adapter provides a socket for detachable connection of companion structures.

6. The implant system as set forth in claim 1 in which said anchor is sized so that its upper end is located substantially at the level of the top of the alveolar ridge whereby the axis of bending of the adapter is at the level of the gum tissue thus minimizing the turning torque upon said adapter as a result of occlusal forces.

7. The implant system as set forth in claim 1 in which said adapter is made of commercially pure titanium.

8. The implant system as set forth in claim 1 in which said adapter is made of a titanium alloy or about 90% titanium, 6% aluminum and 4% vanadium.

9. The implant system of claim 1 wherein said neck portion is cylindrical-shaped or frustoconical-shaped.

10. In a dental implant system:
    (a) an anchor adapted to be secured to the bone tissue at the alveolar ridge of a subject with an orientation determined by case study;
    (b) an adapter having two ends, one end being connected to the anchor and the other end projecting from the anchor; said adapter having a neck portion which is located adjacent the top of said anchor, said neck portion having a size and shape adapted to permit bending the projecting end substantially at the level of the top of the alveolar ridge without distorting, breaking or weakening said neck portion, whereby the axis of bending of the projecting end is at the level of the gum tissue thus minimizing the turning torque upon said adapter as a result of occlusal forces, said neck portion providing a transverse axis for bending of the projecting end to change the angularity of said projecting end from that of said connected end so that the attitude of said anchor can be selected to maximize retention without compromising desired position of a prosthesis to be joined to said projecting end to achieve optimum aesthetics and/or function.

11. The implant system as set forth in claim 10 in which said adapter is made of commercially pure titanium with a neck diameter between 0.060 and 0.090 inches.

12. The implant system as set forth in claim 10 in which said adapter is made of a titanium alloy of about 90% titanium, 6% aluminum and 4% vanadium with a neck diameter between 0.050 and 0.080 inches.

13. The implant system as set forth in claim 10 in which said projecting end of said adapter provides a coping upon which a tooth restoration may be built.

14. The implant system as set forth in claim 10 in which said projecting end of said adapter provides a socket for detachable connection of companion structures.

15. The implant system as set forth in claim 10 in which said adapter is made of commercially pure titanium.

16. The implant system as set forth in claim 10 in which said adapter is made of a titanium alloy or about 90% titanium, 6% aluminum and 4% vanadium.

17. In a dental implant system:
    (a) an anchor adapted to be secured to the bone tissue at the alveolar ridge of a subject with an orientation determined by case study;
    (b) an adapter having two ends, one end being connected to the anchor and the other end projecting from the anchor; said adapter having a neck portion which is located adjacent the top of said anchor, said neck portion having a size and shape adapted to permit bending the projecting end substantially at the level of the top of the alveolar ridge without distorting, breaking or weakening said neck portion, whereby the axis of bending of the projecting end is at the level of the gum tissue thus minimizing the turning torque upon said adapter as a result of occlusal forces.

* * * * *